United States Patent [19]
Yoshida et al.

[11] Patent Number: 5,358,849
[45] Date of Patent: Oct. 25, 1994

[54] MONOCLONAL ANTIBODY RECOGNIZING MEMBRANE PHOSPHOLIPASE $A_2$ AND IMMUNOASSAY OF MEMBRANE PHOSPHOLIPASE $A_2$

[75] Inventors: Nobuo Yoshida; Misao Ide, both of Hyogo; Masao Kono, Osaka; Akiko Kanda, Hyogo, all of Japan

[73] Assignee: Shionogi & Co., Ltd., Osaka, Japan

[21] Appl. No.: 53,350

[22] Filed: Apr. 28, 1993

Related U.S. Application Data

[63] Continuation of Ser. No. 697,008, May 8, 1991, abandoned.

[30] Foreign Application Priority Data

May 30, 1990 [JP] Japan ................... 2-142462

[51] Int. Cl.$^5$ ............. G01N 33/573; G01N 33/541; C07K 15/28; C12N 5/16
[52] U.S. Cl. ..................... 435/7.4; 435/7.23; 435/7.94; 435/70.21; 435/240.27; 436/64; 436/540; 436/548; 530/388.26; 530/391.3
[58] Field of Search .............. 435/7.4, 7.23, 7.94, 435/70.21, 188, 240.27; 436/64, 813, 540, 548; 530/388.26, 809, 391.3

[56] References Cited

FOREIGN PATENT DOCUMENTS 2286081 11/1990 Japan .

OTHER PUBLICATIONS

Nevalainen, T. J. et al, Clin. Chem. 31(7):1116–11120 1985.
Yolken, R. H. 1985. "Solid Phase immunoassys for the detection of viral diseases" ch 9 in *Immunochemistry of viruses* eds M. H. V. van Regenmortel & A. R. Neurath, Elsevier Science Publ.
Yelton & Scharff 1981 "Monoclonal Antibodies: A Powerful New Tool in Biology and Medicine" Ann Rev. Biochem 30:657–680.
Biochemical and Biophysical Research Communications, vol. 162, No. 3, pp. 1030–1036 (1989), Ishizaki et al.
de Jong et al, Eur. J. Biochem., vol. 164, No. 1, pp. 129–135 (1987).
Aarsman et al., The Journal of Biological Chemistry, vol. 264, No. 17, pp. 10008–10014 (1989).
Ogawa et al, Gendai Iryou, vol. 20, pp. 3013–3017 (1988).
Van den Bosch, Phospholipids, Chapter 9, pp. 313–357 (1982).
Van den Bosch, Biochim. Biophys. Acta. vol. 604, pp. 191–246 (1980).
Vadas et al., Lab Invest., vol. 55, pp. 391–404 (1986).
Kanda et al., Biochem. Biophys. Res. Commun., vol. 163, pp. 42–48 (1989).
Nakano et al, FEBS Lett., vol. 261, pp. 171–174 (1990).
Kramer et al., J. Biol. Chem., vol. 264, pp. 5768–5775 (1989).

*Primary Examiner*—Esther M. Kepplinger
*Assistant Examiner*—Nancy J. Parsons
*Attorney, Agent, or Firm*—Birch, Stewart, Kolasch & Birch

[57] ABSTRACT

The present invention first provides monoclonal antibodies recognizing membrane phospholipase $A_2$, namely, monoclonal antibodies PL-49, PL-71, PL-76, and PL-78, hybridomas producing them, methods for producing them, and immunoassays of membrane phospholipase $A_2$ using them.

The immunoassay of PLA$_2$M is useful for the diagnosis of articular rheumatism, cancers, and a wide variety of inflammatory states.

16 Claims, 6 Drawing Sheets

Gel-Filtration of 125I-labeled PLA₂M

FIG. 3

Standard Curve of RIA of PLA₂M

FIG. 4

Dilution Curve of Human Serum

FIG. 5

Ion Exchange Chromatogram of
Standard PLA$_2$M and Articular Rheumatic's
Serum

FIG. 6

Serum PLA₂ in Normal Persons and Patients

MONOCLONAL ANTIBODY RECOGNIZING MEMBRANE PHOSPHOLIPASE A$_2$ AND IMMUNOASSAY OF MEMBRANE PHOSPHOLIPASE A$_2$

This application is a continuation of application Ser. No. 07/697,008 filed on May 8, 1991, now abandoned.

BACKGROUND OF THE INVENTION

1. Field of the Invention

The present invention relates to monoclonal antibodies recognizing membrane phospholipase A$_2$; hybridomas producing said monoclonal antibodies; a method for producing said monoclonal antibodies; and immunoassays using said monoclonal antibodies.

2. Description of the Prior Art

Phospholipase A$_2$ (PLA$_2$) (EC 3.1.1.4) is an enzyme which can hydrolyze the fatty acyl ester bond at the sn-2 position of glycerophospholipids. It is well known that the enzyme is present in the pancreas or snake venom, and it has been observed that the level of pancreatic PLA$_2$ in blood becomes increased when suffering from pancreatitis (Ogawa et al., Gendai Iryou, 20 (1988) 3013–3017). The PLA$_2$, however, is not only present in the external secretion system, but also found in almost all of the cells in a living body, although the amount thereof is very small (Van den Bosch, H. in Phospholipids (Hawthrone, J. N. and Ansell, G. B. eds.) (1982) pp. 313–357, Elsevier/North-Holland Biomedical Press, Amsterdam). It is believed that the enzyme would play an important role in the metabolic regulation of membrane phospholipids and in the eicosanoide biosynthesis through arachidonic acid (Van den Bosch, H., Biochim. Biophys. Acta (1980) 604, 191–246), and would relate to inflammation and cellular injury through the direct action or through its metabolites such as lysophospholipids, leukotrienes, platelet-activating factor and lipid peroxides (Vades, P. et al., Lab Invest. (1986) 55, 691–404).

It was revealed that membrane PLA$_2$ (PLA$_2$M) isolated from human splenic membrane fraction was the different type of PLA$_2$ from pancreatic PLA$_2$ by analysis of its protein primary structure (Kanda, A. et al., Biochem. Biophys. Res. Commun. (1989) 163, 42–48), and it was also found that PLA$_2$M was induced by an inflammatory mediator such as IL-1 and TNF and secreted out of the cells (Nakano, T. et al., FEBS Lett. (1990) 261, 171–174). Moreover, a comparison between PLA$_2$M and PLA$_2$ purified from rheumatoid arthritic synovial fluid showed that they are identical in their structure and reactivity (Kramer, R. M. et al., J. Biol. Chem. (1989) 264, 5768–5775).

From a clinical point of view, an increase of the PLA$_2$ enzymatic activity was found in the blood of patients with an infectious disease such as septicemia, pustular psoriasis, Crohn's disease, and rheumatoid arthritis. Further, it was found that the PLA$_2$ enzymatic activity is induced by intracutaneous injection of bacteria, viruses, or other inflammatory inducers into an animal (Vades, P. et. al., supra).

To date, however, no report has appeared concerning the assay of PLA$_2$M, and it has not yet been shown whether an increase of the PLA$_2$ enzymatic activity accompanying the aforesaid diseases is caused by PLA$_2$M or not.

As described above, because the PLA$_2$ enzymatic activity in blood is increased when suffering from rheumatism, septicemia, pustular psoriasis, Crohn's disease, or the like, it has been expected that the diagnosis of these diseases can be realized from the measurement of PLA$_2$M and an assay of PLA$_2$M has been desired.

SUMMARY

The present invention first provides monoclonal antibodies recognizing membrane phospholipase A$_2$, namely, monoclonal antibodies PL-49, PL-71, PL-76, and PL-78. The membrane phospholipase A$_2$ is preferably derived from human spleen. The present invention further provides hybridomas producing the monoclonal antibodies. The monoclonal antibodies can be produced by growing the hybridomas in the abdominal cavity of a mouse and separating the monoclonal antibodies from the ascitic fluid accumulated in the abdominal cavity. The present invention also provides an immunoassay of membrane phospholipase A$_2$ using the monoclonal antibodies. Preferred immunoassay is a radioimmunoassay. In a sandwich immunoassay, an enzymeimmunoassay is preferable.

The immunoassay of PLA$_2$M using the monoclonal antibodies is useful not only for the diagnosis of articular rheumatism but also for the diagnosis of cancers and a wide variety of inflammatory states including an external wound.

DETAILED DESCRIPTION OF THE INVENTION

The present invention provides monoclonal antibodies recognizing membrane phospholipase A$_2$. The membrane phospholipase A$_2$ is preferably derived from human spleen, as described in Biochem. Biophys. Res. Commun. Vol. 163, No. 1, 1989, pp. 42–48. In the present invention, monoclonal antibody PL-49, monoclonal antibody PL-71, monoclonal antibody PL-76, and monoclonal antibody PL-78 were obtained as detailed in Examples below.

The present invention further provides hybridomas producing the corresponding monoclonal antibodies described above. The hybridoma PL-49, hybridoma PL-71, hybridoma PL-76, and hybridoma PL-78 can produce monoclonal antibody PL-49, monoclonal antibody PL-71, monoclonal antibody PL-76, and monoclonal antibody PL-78, respectively. These hybridoma PL-49, hybridoma PL-71, hybridoma PL-76, and hybridoma PL-78 were deposited on May 9, 1990, under the terms of the Budapest Treaty with Fermentation Research Institute, Agency of Industrial Science and Technology, 1-3, Higashi 1 chome, Tsukuba-shi, Ibaraki-ken, 305 Japan, and have been assigned House hybridoma PL-49 with the Accession No. FERM BP-2891, House hybridoma PL-71 with the Accession No. FERM BP-2892, Mouse hybridoma PL-76 with the Accession No. FERM BP-2889, and Mouse hybridoma PL-78 with the Accession No. FERM BP-2890, respectively.

The aforesaid monoclonal antibodies can be produced by growing the corresponding hybridomas described above in the abdominal cavity of a mouse, and separating the monoclonal antibodies from the ascitic fluid accumulated in the abdominal cavity.

The present invention also provides an immunoassay of membrane phospholipase $A_2$ using the aforementioned monoclonal antibodies. Preferred immunoassay is radioimmunoassay. In the immunoassay where the membrane phospholipase $A_2$ is sandwiched between two different species of the aforesaid monoclonal antibodies, an enzyme immunoassay is preferable.

EXAMPLE 1

Preparation of monoclonal antibodies against membrane $PLA_2$ ($PLA_2M$)

(1) Immunization

The method for preparing $PLA_2M$ used in the immunization and the assay of antibodies was as described in Biochem. Biophys. Res. Commun. Vol. 163, No. 1, 1989, pp. 42–48.

First immunization: a solution of $PLA_2M$ in phosphate-buffered saline (PBS) was mixed with Freund's Complete Adjuvant (FCA) to form an emulsion in a ratio of 1:1. The emulsion was administered subcutaneously to eight mice (Balb/C, female, 12 weeks old) at a dose equivalent to 2 μg of protein for each mouse.

Second immunization: it was carried out 23 days after the first immunization in the same manner as that of the first immunization.

Third immunization: it was carried out 44 days after the second immunization in the same manner as that of the first immunization.

Fourth immunization: it was carried out 81 days after the third immunization in the same manner as that of the first immunization.

(2) Determination of serum titer

The level of anti-$PLA_2$ M antibody in the blood of the immunized animals was determined by ELISA. That is, 0.5 ng of $PLA_2M$ in 0.1 ml of 0.1 M $NaHCO_3$ was added to each well of a microtiter plate and left overnight at 4° C. to coat the plate, after which 0.3 ml of 1% bovine serum albumin (BSA) in PBS was added thereto and the mixture was incubated at 37° C. for 1 hour to block the plate. Then, 0.05 ml of a sample was added and allowed to react at 37° C. for 1 hour, followed by an assay with a Vectastain ABC kit (mouse IgG kit, Vector Laboratories, Inc.) according to its protocol. As a color former, 1 mg/ml of ortho-phenylenediamine (OPD) was used and the difference in absorbances at 492 nm and at 660 nm was determined by a Corona microplate photometer MTP-22. The mice exhibiting a high $PLA_2M$ antibody titer were used for hybridoma preparation.

(3) Preparation of hybridomas (3.1) Experiment 1

Thirty-one days after the fourth immunization, fifth immunization was carried out. Four micrograms of $PLA_2M$ was dissolved in 0.2 ml of PBS and the resulting solution was administered intraperitoneally to the mice. Three days after the fifth immunization, a cell fusion was carried out. The method for the cell fusion was substantially the same as that of Galfre and Milstein (Methods Enzymol. 73, 46 (1981)). That is, mouse myeloma cells (P3X63-Ag8.653) were cultured in an RPMI1640 medium (90% RPMI1640; 10% fetal calf serum; 0.15 mg/ml sodium pyruvate; 0.15 mg/ml oxaloacetic acid; and 0.1 mg/ml kanamycin). From the resulting culture, $4.67 \times 10^7$ mouse myeloma cells were harvested and mixed with $9.33 \times 10^7$ spleen cells of the immunized mice, and the combined cells were pelleted by centrifugation in a centrifugation tube and 1 ml of 48% polyethylene glycol 4000 solution was added dropwise over 1 minute. The mixture was then stirred for 1.5 minutes, followed by slow addition, in a dropwise fashion with stirring, of a serum-free RPMI1640 medium in an amount of 2 ml over 2 minutes, 2 ml over 1 minute, and 6 ml over 2 minutes. Finally, 15 ml of the same medium was gently added and the mixture was pelleted by centrifugation. The pellets obtained were suspended in an HAT medium (70% RPMI1640; 10% NCTC109; 20% fetal calf serum; $10^{-4}$M hypoxanthine; $4 \times 10^7$M aminopterin; $1.6 \times 10^{-5}$M thymidine; 0.15 mg/ml sodium pyruvate; 0.15 mg/ml oxaloacetic acid; 0.2 IU/ml insulin; $2.5 \times 10^{-4}$M 2-mercaptoethanol; $5 \times 10^{-3}$M HEPES; 0.1 mg/ml kanamycin; and nonessential amino acids). The suspension was adjusted to have a concentration of $0.75 \times 10^6$ spleen cells per milliliter and then dispensed as 0.2 ml portions into each well of 96-well plates. The plates were incubated in 95% air-5% $CO_2$ at a temperature of 37° C. and humidity of 95% or more, and the medium was replaced, if necessary, half by half with a fresh HAI medium.

(3.2) Experiment 2

Thirty-five days after the fourth immunization, fifth immunization was carried out in the same manner as in Experiment 1. Three days after the fifth immunization, a cell fusion was carried out. As the mouse myeloma cell strain, $8.89 \times 10^7$ P3X63-Ag.8.653 cells were used for the cell fusion with $1.7 \times 10^8$ mouse spleen cells in the same manner as in Experiment 1. The cells subjected to the cell fusion were suspended in an HAI medium to have a concentration of $0.63 \times 10^6$ cells/ml, and the suspension was then dispensed as 0.2 ml portions into each well of 96-well plates, followed by incubation in the same manner as in Experiment 1.

(4) Screening of hybridomas

After about 2 weeks the culture supernatant of hybridomas which grew was examined whether anti-$PLA_2M$ antibodies were produced therein or not. The assay was carried out in the same manner as that of Item (2). Four hybridomas (PL-49, PL-71, PL-76 and PL-78) each of which stably produced an antibody having a specific reactivity with $PLA_2M$ were obtained by the screening.

(5) Cloning of hybridomas and storage in frozen state

The aforesaid four hybridoma cells were cloned by a limiting dilution technique. That is, each of the hybridomas was suspended in an RPMI1640 medium and the suspension was added to a 96-well plate to have a concentration of 0.3 cells in 0.2 ml for each well, followed by incubation. The anti-$PLA_2M$ antibody titer of the culture supernatant was determined in the same manner as that of Item (4). The anti-$PLA_2M$ antibody-producing hybridomas were selected and grown, after which they were stored under freezing in a freezing solution (90% fetal calf serum and 10% dimethylsulfoxide).

(6) Preparation of ascitic fluid

To each group of mice (Balb/C, female, 10–15 weeks old) to which 0.5 ml of pristane had been administered intraperitoneally before 7–10 days, a suspension of each of the hybridoma cells in PBS ($2$–$5 \times 10^6$ cells/ml) was administered intraperitoneally at a dose of 0.5 ml for each mouse. After about 1 week, an ascitic fluid accumulated in the respective mice was collected by a tapping technique. From the ascitic fluid collected, precipitate was removed by centrifugation using a Separapid tube (SEKISUI KAGAKU). The ascitic fluid so treated was dispensed and stored under freezing.

(7) Determination of antibody class and subclass

The immunoglobulin class and subclass of the monoclonal antibodies produced by the respective hybridomas were determined by ELISA. A mouse MonoAb-ID-EIA kit (Zymed Co., Ltd.) was used for the determination. In all cases of four hybridomas, PL-49, PL-71, PL-76 and PL-78, immunoglobulins produced thereby were identified as $IgG_1$ ($\gamma 1$, $\kappa$).

(8) Purification of antibodies

The monoclonal antibodies were purified from the ascitic fluid by the use of an Affigel protein A MAPS II kit (Bio-Rad Co., Ltd.) according to its protocol.

(9) Preparation of peroxidase conjugate

According to the method of Nakane et al. (J. Histochem. Cytochem., 22, 1084 (1974)), a conjugate of PL-71 with horseradish peroxidase was prepared. First, 0.1 ml of 0.1M $NaIO_4$ was mixed with peroxidase (2 mg/0.5 ml in water) and the mixture was allowed to react at room temperature for 20 minutes. The reaction mixture was dialyzed overnight at 4° C. against 1 mM sodium acetate buffer and then adjusted to pH 9.5 with 0.2M $Na_2CO_3$, followed by addition of PL-71 (4 mg/ml in 0.01M $NaHCO_3$). The mixture was then stirred at room temperature for 2 hours and 50 µl of $NaBH_4$ (4 mg/ml in water) was added thereto. The mixture was also stirred at 4° C. for 2 hours and dialyzed overnight at 4° C. against PBS to give the desired conjugate.

(10) Sandwich assay of $PLA_2M$

Figure 1:
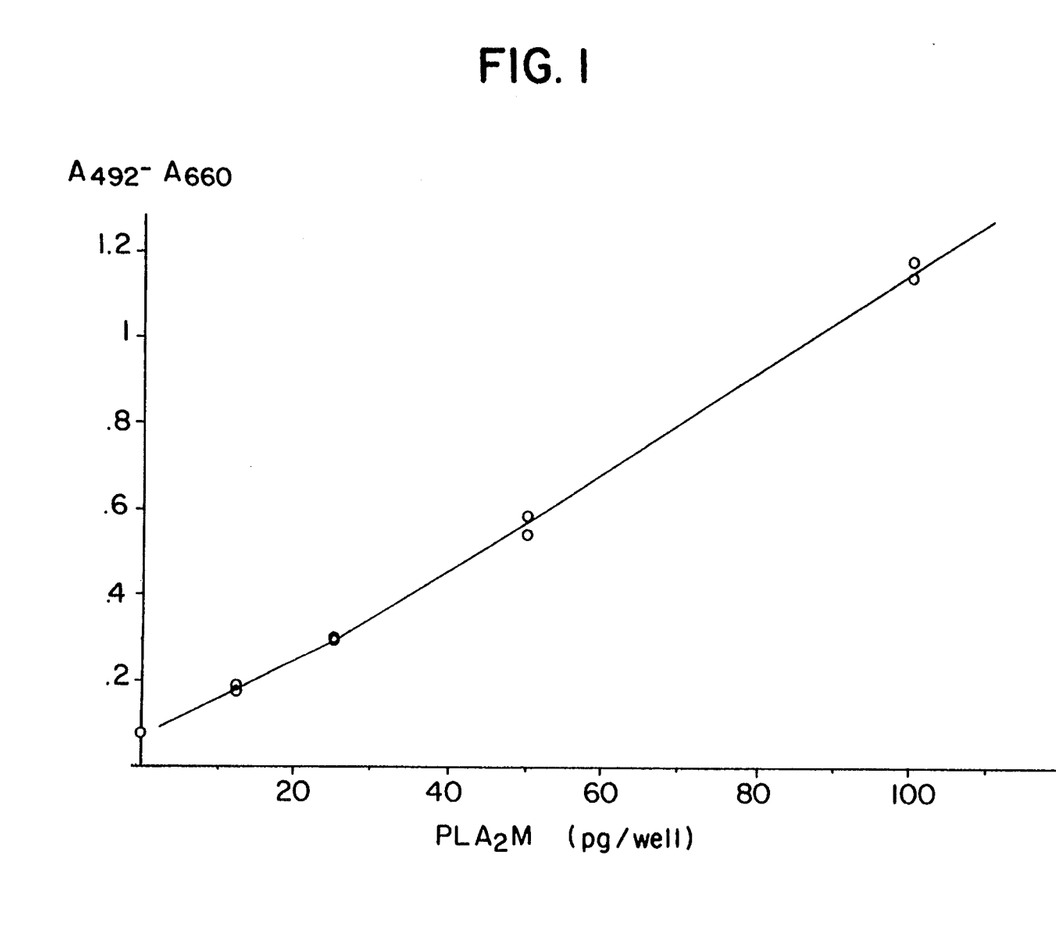
FIG. 1 shows a calibration curve for PLA$_2$M in the sandwich assay using PL-78 and PL-71-peroxidase conjugate.

A solution of monoclonal antibody (PL-78) was added to each well of a microtiter plate (at a concentration of 0.1 µg in 0.1 ml of $NaHCO_3$ for each well). After standing overnight at 4° C., 0.3 ml of PBS containing 1% BSA was added to the plate, which was then incubated at 37° C. for 1 hour, thereby blocking the plate. Thereafter, 0.05 ml of $PLA_2M$ solution (1% BSA in PBS) was added to the plate and allowed to react at 37° C. for 1 hour. Then, 0.05 ml of an 1,000-fold dilution of the peroxidase conjugate with monoclonal antibody PL-71 was added to the plate and allowed to react at 37° C. for 2 hours. Thereafter, ortho-phenylenediamine (at a concentration of 1 mg in 0.1 ml of 0.1M citrate buffer, pH 4.2) and $H_2O_2$ (at a final concentration of 0.03%) were added to the plate and allowed to react at room temperature for 30 minutes. Finally, the reaction was stopped by adding 0.1 ml of 1N $H_2SO_4$ and the difference in absorbances at 492 nm and at 660 nm was measured. FIG. 1 shows a calibration curve of $PLA_2$ M in the sandwich assay using PL-78 and the peroxidase conjugate with PL-71. The sensitivity for detecting $PLA_2M$ by the present method was approximately 0.01 ng/well (see FIG. 1).

EXAMPLE 2

Radioimmunoassay (RIA) of membrane phospholipase $A_2$ ($PLA_2M$)

(1) Preparation of $^{125}I$-labeled $PLA_2M$

The $^{125}I$-labeled $PLA_2M$ was obtained by a chloramine T technique in accordance with the Hunter-Greenwood method (Nature, 194, 495–496 (1962)).

① Reagents $PLA_2M$ solution: 111 µg/ml in 0.5M phosphate buffer (PB) (pH 7.4), $Na^{125}I$ solution: 3.7 GBq/ml in dilute NaOH solution (pH 7–11)

Chloramine I solution; 2 mg/ml in 0.5M PB (pH 7.4),

Sodium pyrosulfite solution: 2.5 mg/ml in 0.1M PB (pH 7.4),

BSA: 10 mg/ml in 0.1M PB (pH 7.4)

② Procedure

Figure 2:
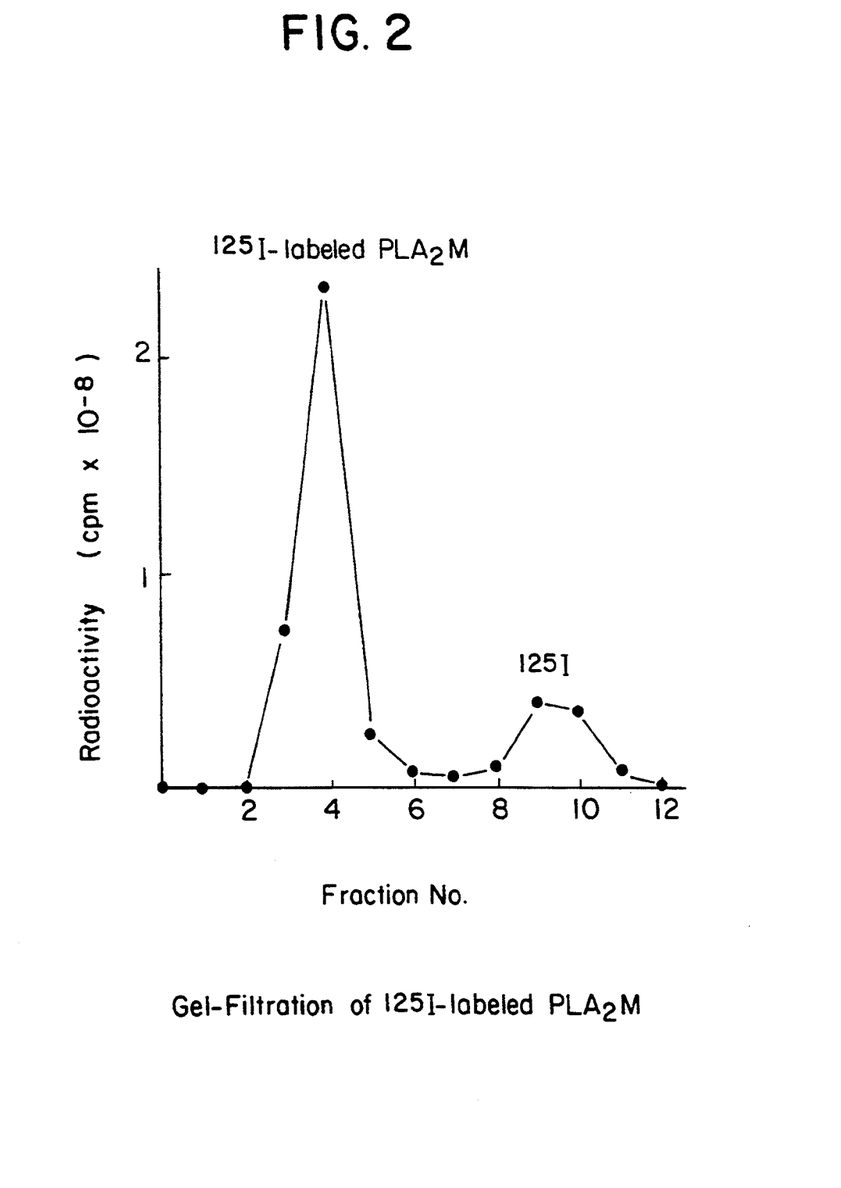
FIG. 2 shows a chromatogram obtained in the gel filtration of $^{125}$I-labeled solution of PLA$_2$M.

First, 25 µl of 0.5M PB (pH 7.4) and 22.5 µl of the $PLA_2M$ solution were taken in a polypropylene tube, after which 2.5 µl of the $Na^{125}I$ solution was added and the contents were mixed well together. Then, 2.5 µl of the chloramine T solution was also added and the contents were stirred at room temperature for 50 seconds. To this tube, 12.5 µl of the sodium pyrosulfite solution was further added and the contents were stirred, after which 2.5 µl of BSA and 2.5 µl of potassium iodide solution were added and the contents were mixed well together. The resulting mixture was then subjected to gel filtration (the column was PD-10 (manufactured by Pharmacia Co., Ltd.); the eluent was 0.1M PB (pH 7.5) containing 0.5M sodium chloride, 0.5% BSA, and 0.05% sodium azide), and 1 ml-fractions of the eluate were collected. The radioactivity of each fraction was measured by means of a well-type scintillation counter. The chromatograms obtained are shown in FIG. 2. Fraction No. 4 in this figure was identified as $^{125}I$-labeled $PLA_2M$.

(2) RIA of $PLA_2M$

① Reagents $PLA_2M$ standard solution: 0.2–200 ng/ml assay buffer,

Ascitic dilutions: 680,000-, 470,000-, 860,000- and 2,300,000-fold dilutions of PL-49, PL-71, PL-76 and PL-78, respectively, with the assay buffer, $^{125}I$-labeled $PLA_2M$ solution: a dilution of the labeled solution as described in Item (1) with the assay buffer ($2 \times 10^6$ cpm/ml), Immunobead liquid: a suspension of rabbit anti-mouse immunoglobulin-bound polyacrylamide gel (manufactured by Bio-Rad Co., Ltd.) in the assay buffer (1 mg/ml), Assay buffer: 0.1M PB (pH 7.5) containing 0.5M sodium chloride, 1 mM ethylenediaminetetraacetic acid, 0.5% BSA, and 0.02% sodium azide.

② Procedure

First, 100 µl of the $PLA_2M$ standard solution or a serum sample was taken in a polypropylene tube, after which 275 µl of the assay buffer and 25 µl of the $^{125}I$-labeled $PLA_2M$ solution were added and the contents were mixed well together. Then, 100 µl of the ascitic fluid dilution was also added and the contents were incubated at room temperature for 16 hours. To this tube 100 µl of the immunobead liquid was further added and the contents were incubated at room temperature for 1 hour, followed by centrifugation ($2000 \times g$, 10 min). After the removal of the supernatant by suction, the radioactivity of the precipitate was measured by means of a well-type scintillation counter. Based on the readings from a standard curve obtained by the use of the $PLA_2M$ standard solution, a concentration of $PLA_2M$ in the serum sample was determined.

③ Standard curve and sensitivity

Figure 3:
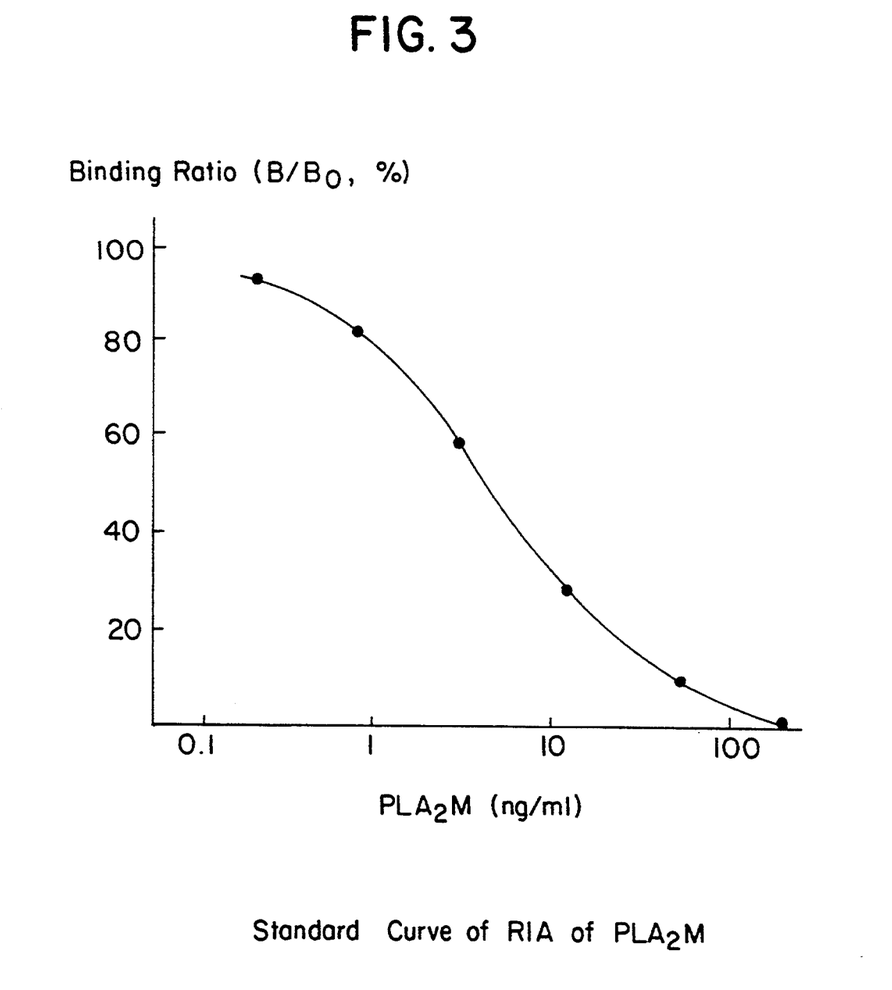
FIG. 3 shows a standard curve in the RIA of PLA$_2$M.

FIG. 3 shows a standard curve obtained in the RIA when PL-49 was used as an ascitic fluid. Other ascitic fluids gave similar competition curves. The sensitivity (i.e., concentration for 90% inhibition) was 0.3 ng/ml for PL-49, 1.1 ng/ml for PL-71, 0.9 ng/ml for PL-76 and 0.2 ng/ml for PL-78, all of which were considered to be highly sensitive.

④ Specificity

Figure 4:
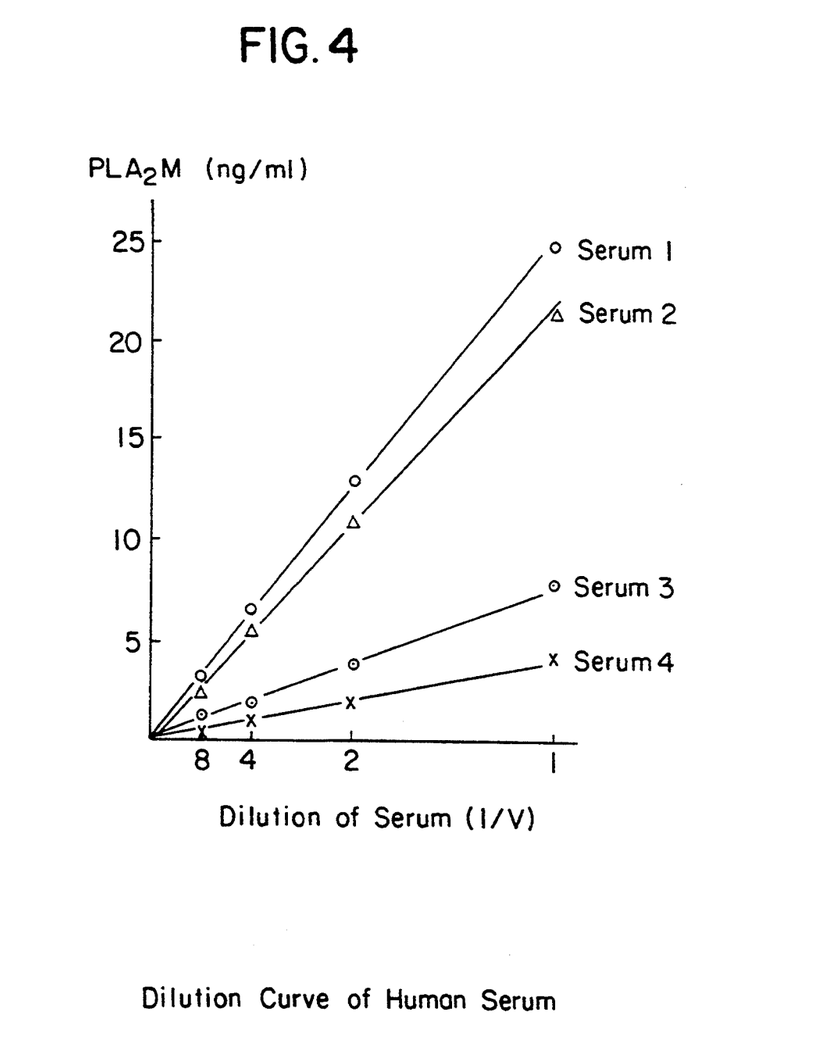
FIG. 4 shows a dilution curve for human sera.

As shown in FIG. 4, all the dilution curves for human sera obtained by the present method exhibited a good liner regression and there appeared no influence of sera on the curves.

Moreover, no cross reaction of human pancreas $PLA_2$ was observed in the present method.

Figure 5:
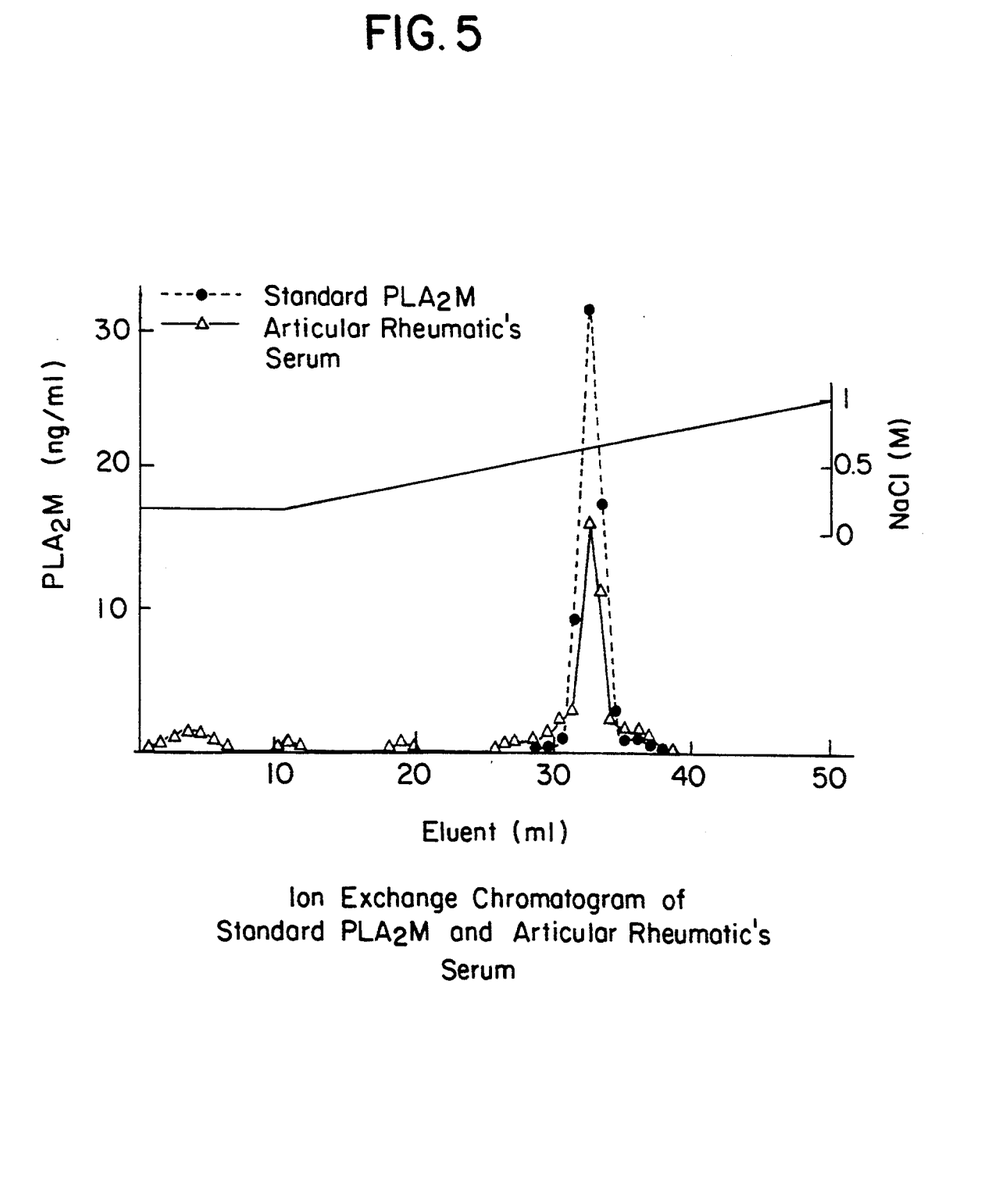
FIG. 5 shows the results of ion exchange chromatography of the standard PLA$_2$M and sera from patients with articular rheumatism.

In addition, standard $PLA_2M$ and sera from patients with articular rheumatism were subjected to ion exchange chromatography (column was S-Sepharose Fast Flow Type (manufactured by Pharmacia Co., Ltd.); eluent was 50 mM Tris buffer (pH 7.0) with a linear gradient containing from 0.2 to 1M sodium chloride and 0.1% CHAPS (manufactured by Dotite Co., Ltd.)). The eluate was fractionated and $PLA_2M$ present in each fraction was measured by the present method. The results provided a chromatogram as shown in FIG. 5, indicating that the pattern of the chromatogram obtained by the standard $PLA_2M$ had a good fit to that obtained by the sera of patients.

These results revealed that the present method is applicable to a specific assay of $PLA_2M$ present in human sera.

⑤ Assay of human sera

Figure 6:
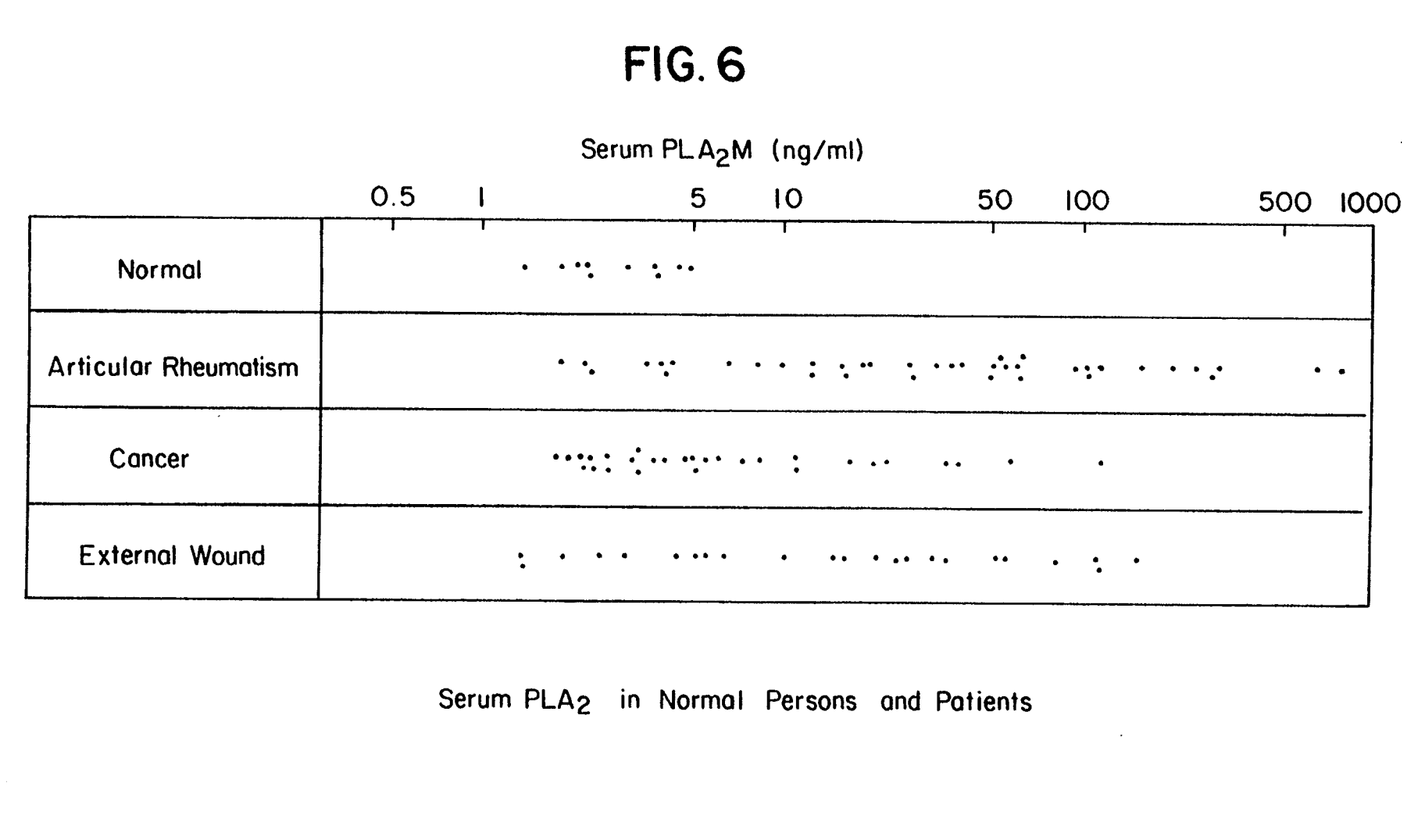
FIG. 6 shows the concentrations of PLA$_2$M in sera from normal individuals, patients with articular rheumatism, patients with cancer, and patients with an external wound.

According to the present method, various sera from normal individuals, patients with articular rheumatism, patients with cancer, and patients with an external wound were applied to the assay of $PLA_2M$ in an undiluted or appropriately diluted form with the assay buffer. The results are shown in FIG. 6. As seen from this figure, many of serum samples from patients with articular rheumatism, patients with cancer, and patients with an external wound exhibited a higher level of $PLA_2M$ than that of the serum sample from normal individuals, indicating that the present method is useful for the diagnosis of articular rheumatism and cancers.

What we claim is:

1. A hybridoma having all of the identifying characteristics of FERM BP-2891.
2. A hybridoma having all of the identifying characteristics of FERM BP-2892.
3. A hybridoma having all of the identifying characteristics of FERM BP-2889.
4. A hybridoma having all of the identifying characteristics of FERM BP-2890.
5. A monoclonal antibody secreted by a cell line selected from the group consisting of the hybridoma FERM BP-2889, hybridoma FERM BP-2890, hybridoma FERM BP-2891 and hybridoma FERM BP-2892.
6. An antibody secreted by the hybridoma of claim 1.
7. An antibody secreted by the hybridoma of claim 2.
8. An antibody secreted by the hybridoma of claim 3.
9. An antibody secreted by the hybridoma of claim 4.
10. An immunoassay for the detection of human spleen membrane phospholipase $A_2$, which comprises the steps of:
    i) contacting a sample suspected of containing human spleen membrane phospholipase $A_2$ with an antibody according to claim 5, under conditions which promote binding of said antibody to said human spleen membrane phospholipase $A_2$; and
    ii) detecting binding of said antibody to said human spleen membrane phospholipase $A_2$.
11. An immunoassay according to claim 10, wherein said antibody is labelled with a radioisotope and said detecting is performed by detecting emission from said radioisotope.
12. An immunoassay according to claim 10, wherein said detecting is performed by contacting said human spleen membrane phospholipase $A_2$ bound to said antibody with a second antibody secreted by a cell line selected from the group consisting of hybridoma FERM BP-2889, hybridoma FERM BP-2890, hybridoma FERM BP-2891, and hybridoma FERM BP-2892 containing a label, wherein said second antibody is not the same as the antibody in step (i), and detecting said label.
13. The immunoassay according to claim 12, wherein said label is peroxidase.
14. A method for screening for cancer, which comprises:
    i) obtaining a serum sample from a subject;
    ii) contacting said serum sample with a monoclonal antibody of claim 5, under conditions which promote binding of said antibody to human spleen membrane phospholipase $A_2$;
    iii) detecting the binding of said antibody to said human spleen membrane phospholipase $A_2$; and
    iv) comparing the amount of antibody bound in step iii) with the amount bound to human spleen membrane phospholipase $A_2$ in serum samples obtained from normal subjects, wherein a higher amount of antibody binding suggests the presence of cancer in said subject.
15. An immunoassay for determining the amount of human spleen membrane phospholipase $A_2$ in a sample, which comprises the steps of:
    i) contacting a sample suspected of containing human spleen membrane phospholipase $A_2$ with an antibody according to claim 5 in the presence of radioisotope-labelled human spleen membrane phospholipase $A_2$, under conditions which promote binding of said antibody to said human spleen membrane phospholipase $A_2$;
    ii) measuring binding of said radioisotope-labelled human spleen membrane phospholipase $A_2$ to said antibody; and
    iii) determining the amount of said human spleen membrane phospholipase $A_2$ by referring to a standard curve.
16. An immunoassay for determining the amount of human spleen membrane phospholipase $A_2$ in a sample, which comprises the steps of:
    i) contacting a sample suspected of containing human spleen membrane phospholipase $A_2$ with a first antibody according to claim 5, under conditions which promote binding of said first antibody to said human spleen membrane phospholipase $A_2$ to form a complex;
    ii) contacting said complex of step i) with a second antibody according to claim 5 containing an, wherein said second antibody is not the same as said first antibody, under conditions which promote binding of said second antibody to said human spleen membrane phospholipase $A_2$ to form a further complex;
    iii) removing unbound said second antibody;
    iv) incubating said further complex of step ii) with a substrate of said enzyme label;
    v) determining the amount of enzyme reaction product formed; and
    vi) determining the amount of said human spleen membrane phospholipase $A_2$ by referring to a standard curve.

* * * * *